(12) United States Patent
Rak

(10) Patent No.: US 10,217,376 B2
(45) Date of Patent: Feb. 26, 2019

(54) NUTRITIONAL VALUE OF FOOD

(71) Applicant: Stanley C. Rak, Whitehouse Station, NJ (US)

(72) Inventor: Stanley C. Rak, Whitehouse Station, NJ (US)

( * ) Notice: Subject to any disclaimer, the term of this patent is extended or adjusted under 35 U.S.C. 154(b) by 220 days.

(21) Appl. No.: 14/624,044

(22) Filed: Feb. 17, 2015

(65) Prior Publication Data

US 2016/0240101 A1 Aug. 18, 2016

(51) Int. Cl.
*G09B 19/00* (2006.01)
*G09B 5/02* (2006.01)

(52) U.S. Cl.
CPC ........... *G09B 19/0092* (2013.01); *G09B 5/02* (2013.01)

(58) Field of Classification Search
CPC .................................................. G09B 19/0092
USPC ......................................................... 434/127
See application file for complete search history.

*Primary Examiner* — Kesha Frisby
(74) *Attorney, Agent, or Firm* — Mintz Levin Cohn Ferris Glovsky and Popeo, P.C.

(57) ABSTRACT

A system, a method, and a computer program product for determining a nutritional value of a food item are disclosed. In response to a query from a user, a calorie value of a food item based on a number of calories contained in the food item is determined. Saturated and/or unsaturated fat values of the food item are determined based on a saturated fat value and/or an unsaturated fat value of the food item. A determination of whether at least one vitamin and/or mineral is contained in the food item is made and at least one vitamin and/or mineral value for the food item is generated. A determination is made of whether at least one controversial ingredient is contained in the food item, and at least one controversial ingredient value for the food item is generated. A nutritional value for the food item is generated.

24 Claims, 7 Drawing Sheets

| 0-20% | 0-25% | 0-10% | 0-15% | 0-20% | 0-30% | 75-100% or more | <10% | | |
|---|---|---|---|---|---|---|---|---|---|
| 21-27.9 | 26-33.3 | 11-19.8 | 16-24.3 | 21-26.8 | 31-37.8 | 67.6 | 11-18.8 | 0 | 4 |
| 28-35.9 | 33.4 | 19.9-28.7 | 24.4-32.7 | 26.9 | 37.9 | 74.9 | 18.9 | .7 | 3.7 |
| | 40.7 | | | 32.7 | 44.7 | 60.2 | 26.7 | 1 | 3.3 |
| 36-43.9 | 40.8 | 28.8-37.6 | 32.8-41.1 | 32.8 | 44.8 | 67.5 | 26.8 | 1.3 | 3 |
| 44-51.9 | 48.1 | 37.7-46.5 | 41.2-49.5 | 38.6 | 51.6 | 52.8 | 34.6 | 1.7 | 2.7 |
| | 48.2 | | | 38.7- | 51.7- | 60.1 | 34.7- | 2 | 2.3 |
| | 55.5 | | | 44.5 | 58.5 | 45.4 | 50.3 | 2.3 | 2 |
| 52-59.9 | 55.6- | 46.6-55.4 | 49.6-57.9 | 44.6- | 58.6- | 52.7 | 42.6- | 2.7 | 1.7 |
| | 62.9 | | | 50.4 | 65.4 | 38-45.3 | 50.4 | 3 | 1.3 |
| 60-67.9 | 63-70.3 | 55.5-64.3 | 58-66.3 | 50.5- | 65.5- | 30.6 | 50.5- | 3.3 | 1 |
| | | | | 56.3 | 72.3 | 37.9 | 58.3 | 3.7 | .7 |
| 68-75.9 | 70.4- | 64.4-73.2 | 66.4-74.7 | 56.4- | 72.4- | 23.2 | 58.4- | 4 | 0 |
| | 77.7 | | | 62.2 | 79.2 | 30.5 | 66.2 | | |
| 76-83.9 | 77.8- | 73.3-82.1 | 74.8-83.1 | 62.3- | 79.3- | 15.8- | 66.3- | | |
| | 85.1 | | | 68.1 | 86.1 | 23.1 | 74.1 | | |
| 84-91.9 | 85.2 | 82.2-91 | 83.2-91.5 | 68.2 | 86.2-93 | 8.4 | 74.2 | | |
| | 92.5 | | | 74.1-79 | 93.1-99 | 15.7 | 82.0 | | |
| 92-99.9 | 92.6-99 | 91.1-99 | 91.6-99.9 | 74.1-79 | 93.1-99 | 1-8.3 | 82.1-89 | | |
| 100%+ | 100% | 100% | 100% | 80% | 100% | 0% | 90%+ | | |

Figure 4:
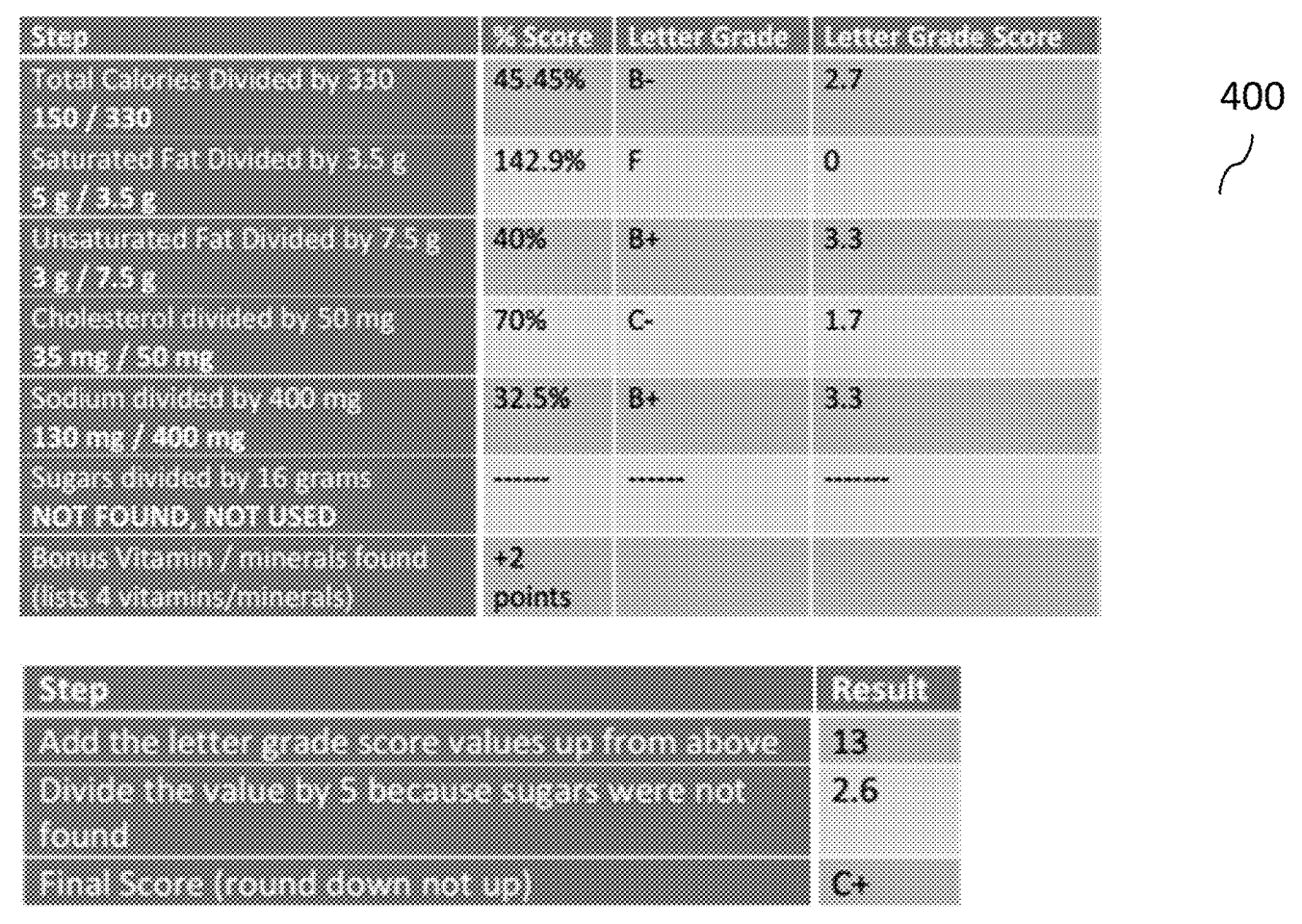

| Stat | % Score | Letter Grade | Letter Grade Score |
|---|---|---|---|
| Total Carbohydrate 159/350 | 45.45% | B- | 2.7 |
| Saturated Fat 10g/7.5g | 142.9% | F | 0 |
| Trans Fat 3g/7.5g | 40% | B+ | 3.3 |
| Sugar 10g/25g | 70% | C- | 1.7 |
| Cholesterol supplied by 400mg 65mg/50mg | 32.5% | B+ | 3.3 |
| Sodium supplied by 1200mg 620mg/400mg | — | — | — |
| Supplemental Vitamins NOT FOUND, NOT USED | — | — | — |
| Extra Vitamins/Minerals Found (Vitamin C, Vitamin B6) | +2 points | | |

| Step | Result |
|---|---|
| Add the letter grade scores from above | 13 |
| Divide the sum by 5 (total stats searched for) | 2.6 |
| Final Score (Look up in table) | C+ |

NUTRITIONAL VALUE OF FOOD

TECHNICAL FIELD

In some implementations, the current subject matter relates to data processing and in particular, to ascertaining a nutritional value of food based on food's constituents.

BACKGROUND

Proper diet plays an important role in maintaining individual's health. Specifically, beneficial dietary choices may reduce development of chronic diseases, weight gain, or other negative effects on a person while improving longevity and overall quality of life. Whereas, poor dietary choices typically have a counter-effect on an individual. The overall diet is determined by a series of individual selections, and thus, proper identification of high or better quality nutritional items is a prerequisite for a healthy diet.

Many food items currently sold in the United States are required to have a "Nutrition Facts" panel as mandated by the Nutrition Labeling and Education Act ("NLEA") and Food and Drug Administration ("FDA"). These panels sometimes provide basic nutritional information and may categorize foods into a "food group" or "food groups." However, such categorization can be imprecise, somewhat misleading or difficult to understand. Additional factors, including serving sizes, mixing with other non-nutritious components (e.g., water), may make it even more difficult to understand the actual nutritional value of a food item being consumed.

Some conventional nutritional systems relate to selection of individual items of food for specific nutritive values, and scoring the aggregate nutritive values of a series of food articles selected for an individual serving of a meal in order to provide an improved form of food-selecting-chart. These methods may generate a sheet on which articles of food are listed in relation to measurements of quantities of their nutrient ingredients in terms of a common rating factor. A common unit measure may be derived by dividing the established measure of the daily requirement per person of each of these items by three, the number of daily meals, and then dividing such quotients by some common arbitrary figure that is selected as representing the number of desired stages in a scoring scale. This provides a fractional scoring unit that is common to individual score scales for the various nutrients that are to be taken into account.

Other conventional methods include enabling individuals to select proper foods for improving health, controlling hunger and managing body weight based on calculations derived from a food's measured nutritional content. These methods involve assigning a ranking to food based on a combination of its calculated nutrient density and a predicted satiating effect. The nutrient density represents a selectively weighted overall nutrient density of the food and is calculated by a formula that yields a numerical rating or scale that proportionately rewards foods that have the highest amount of nutrients per calorie for nutrients that the FDA deems essential. The satiating effect predicts the satiation of a food on a numeric scale. A high effect value indicates that the food will be more satisfying per calorie. The two calculating factors or indices may then be represented and interpreted in an easy to use manner such as on a visual format.

Yet another conventional method involves an iterative algorithm for building a nutritionally balanced list of foods. The algorithm has the following steps: (a) creating an array of values indicating the level of deficiency/surplus in the current food list when compared to a selected standard; (b) comparing each food in a list of favorites to the deficiency/surplus profile, and generating a score for each food indicating the level of match; (c) using the scores to guide a user or algorithm in selecting a food to add to the list; and (d) repeating the above steps until the desired level of compliance is reached.

Other conventional methods also involve rating the nutritional quality of food. These methods include: (a) determining the water free weight percentage of one or more macronutrients in the food item; (b) assigning a numerical influence factor to each of the macronutrients; (c) multiplying the water free weight percentage of each macronutrient by the influence factor of the macronutrient to calculate a nutrient and influence factor product for each macronutrient; and (d) summing the nutrient and influence factor products of the macronutrients to calculate a numerical rating for the food item.

However, the conventional methods do not appear to take into account various assumptions, nutrient weightings, as well as, nutrient, vitamin and ingredient scores that are calculated based on the constituents of a particular food item. Thus, there is a need for a system and method for determining a nutritional health value or score of a food item that uses various inputs, including assumptions based on recommended daily intake ("RDI") value(s) as well as nutrient weightings, to calculate a set of scores relating to nutrients, vitamins and ingredients in a particular food item, where such scores along with other variables are used in several formulas to determine the nutritional value of the food item.

SUMMARY

In some implementations, the current subject matter relates to a computer implemented method for determining a nutritional value of a food item. The method can include determining, in response to a query from a user, using at least one processor coupled to at least one database, a calorie value of a food item based on a number of calories contained in the food item; determining, using the at least one processor coupled to the at least one database, a saturated and/or unsaturated fat values of the food item based on a saturated fat value and/or an unsaturated fat value of the food item; determining, using the at least one processor coupled to the at least one database, whether at least one vitamin and/or mineral is contained in the food item, and based on the determining, generating, using the at least one processor, at least one vitamin and/or mineral value for the food item; determining, using the at least one processor coupled to the at least one database, whether at least one controversial ingredient is contained in the food item, and based on the determining, generating, using the at least one processor, at least one controversial ingredient value for the food item; and generating, using the at least one processor, a nutritional value for the food item based on the determined calorie value, the determined saturated fat value, the determined unsaturated fat value, the generated vitamin and/or mineral value, and the generated controversial ingredient value.

In some implementations, the current subject matter can include at least one of the following optional features. The nutritional value of the food item can be determined based on a 2000-calorie diet for the user. In some implementations, the diet can be based on a higher and/or smaller number of calories. For example, U.S. Department of Agriculture recommends a lower calorie diet for certain individuals, such as, very young children, whose diet can be at least partially based on baby food and/or baby formula. The calorie value can be determined based on a total number of calories contained in the food item and at least one first factor corresponding to a category of food that includes the food item. The saturated and/or unsaturated fat values can be determined based on a total percentage of saturated and/or unsaturated fats contained in the food item and at least one second factor corresponding to a category of food that includes the food item. The vitamins/minerals values can be determined based on a total percentage of vitamins/minerals contained in the food item and at least one third factor corresponding to a category of food that includes the food item. The controversial ingredients values can be determined based on a number of controversial ingredients contained in the food item and at least one fourth factor corresponding to a category of food that includes the food item. The fourth factor can be a constant.

In some implementations, the method can include determining a value of at least one of the following: a potassium value, a sodium value, a sugar value, a cholesterol value, a carbohydrates value, and a fiber value of the food item. The generated nutritional value can be generated based on at least one of the following: the determined potassium value, sodium value, sugar value, cholesterol value, carbohydrates value, and fiber value of the food item.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 3 illustrates exemplary tables that illustrate values that can be stored at the database shown in FIG. 1 and can be used to determine the overall nutritional value of the food item, according to some implementations of the current subject matter;

FIG. 4 illustrates an exemplary numerical calculation for a nutritional food item, according to some implementations of the current subject matter;

DETAILED DESCRIPTION

Figure 1:
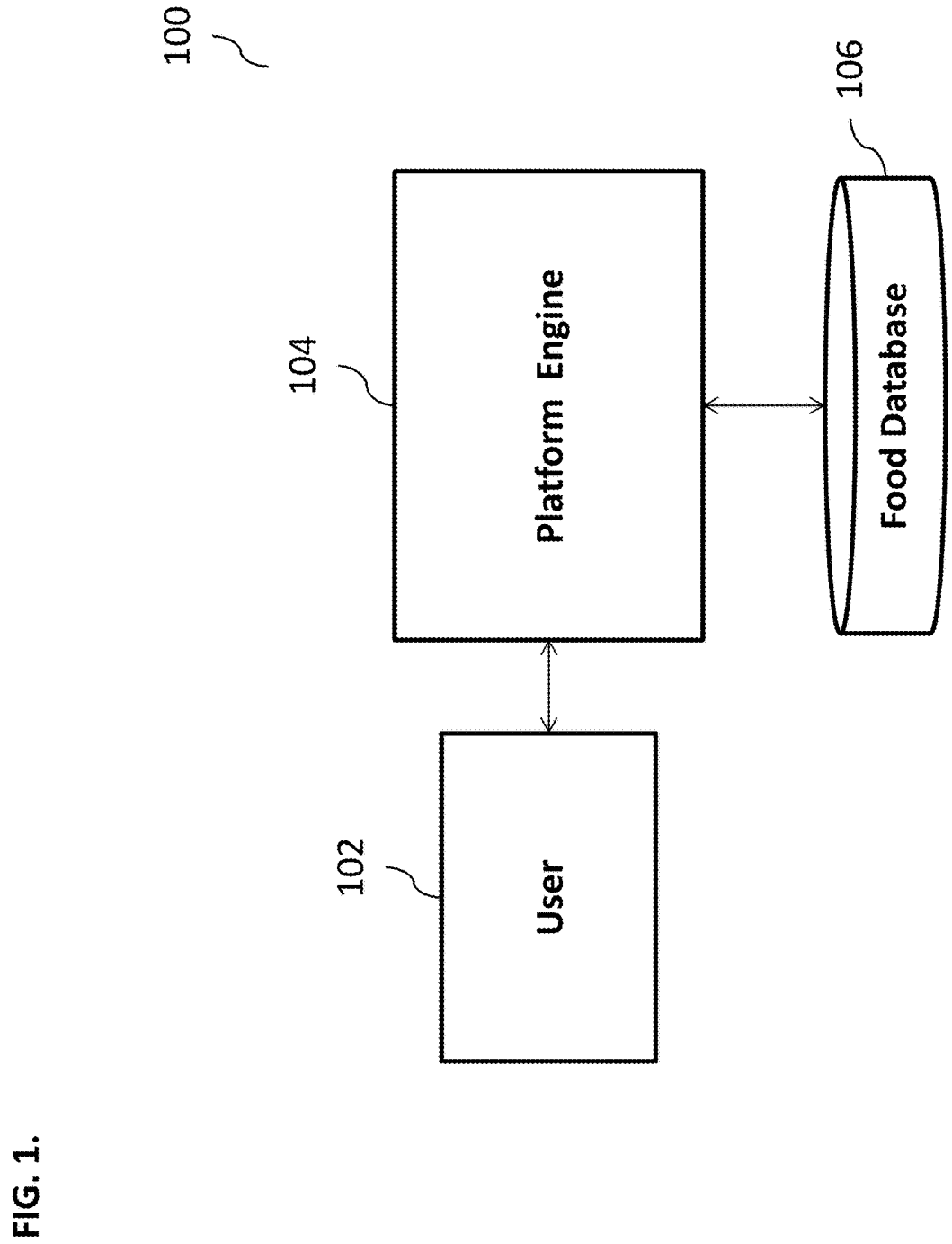
FIG. 1 illustrates an exemplary system for determining a nutritional value of a food item, according to some implementations of the current subject matter.

To address these and potentially other deficiencies of currently available solutions, one or more implementations of the current subject matter provide methods, systems, articles or manufacture, and the like that can, among other possible advantages, provide systems and methods for determining or otherwise ascertaining a nutritional health value or score of a selected food item or items.

In some implementations, the current subject matter relates to a method for determining a nutritional value of a particular food item. In some implementations, the method uses various dietary guidelines as proposed by Food and Drug Administration ("FDA"). In some implementations, these dietary guidelines are based on an assumption that an average individual will consume approximately 2000 calories per day when all his/her daily meals' nutritious values are combined together. In some implementations, the diet can be based on a higher and/or smaller number of calories. For example, U.S. Department of Agriculture recommends a lower calorie diet for certain individuals, such as, very young children, whose diet can be at least partially based on baby food and/or baby formula. Pursuant to the Federal Food, Drug, and Cosmetic Act ("the Act") and accompanying legislation, the FDA has authority to oversee the quality of substances sold as food in the United States, and to monitor claims made in the labeling about both the composition and the health benefits of foods. Substances which the FDA regulates as food are subdivided into various categories, including foods, food additives, added substances (man-made substances which are not intentionally introduced into food, but nevertheless end up in it), and dietary supplements. The specific standards which the FDA exercises differ from one category to the next. Further, the FDA has been granted a variety of means by which it can address violations of the standards for a given category of substances. The Act defines "food" to be: (1) articles used for food or drink for man or other animals, (2) chewing gum, and (3) articles used for components of any such article.

United States Department of Agriculture ("USDA") also provides additional nutrition recommendations in the form of a food guide pyramid. The food guide pyramid suggests optimal nutrition guidelines for each food category, per day, using a mnemonic graphic of a pyramid with horizontal dividing lines to represent suggested percentages of the daily diet for each food group.

Carbohydrates are represented by cereals, bread, pastas, crackers, and rice. Bread, cereal, rice, and pasta are grown from cereal crops. Grains supply food energy in the form of starch and carbohydrates. Breads made from refined ingredients are not as highly recommended as whole grains. Whole grains can be found especially in brown oatmeal. USDA recommends 6-11 servings daily of carbohydrates.

A vegetable is a part of a plant consumed by humans that is generally savory (not sweet) and not considered a grain, fruit, nut, spice, or herb. For example, the stem, root, flower, etc., may be eaten as vegetables. Vegetables contain many vitamins and minerals; however, different vegetables contain different spreads, so it is important to eat a wide variety of types. For example, green vegetables typically contain vitamin A, dark orange and dark green vegetables contain vitamin C, and vegetables like broccoli and related plants contain iron and calcium. Vegetables are very low in fats and calories, but cooking can often add these. USDA recommends 3-5 servings of vegetables in a day. They may be fresh, frozen, canned, or juiced.

In terms of food (rather than botany), fruits are the sweet-tasting seed-bearing parts of plants, or occasionally sweet parts of plants which do not bear seeds. These include apples, oranges, plums, bananas, etc. Fruits are low in calories and fat and are a source of natural sugars, fiber and vitamins. Processing fruits when canning or making into juices unfortunately may add sugars and remove nutrients. The fruit food group is sometimes combined with the vegetable food group. Note that many foods considered fruits in botany because they bear seeds are not considered fruits in cuisine because they lack the characteristic sweet taste, e.g., tomatoes or avocados. It is best to consume 2-4 servings of fruit in a day. They may be fresh, frozen, canned, dried, pureed or juiced.

Dairy products are produced from the milk of mammals, most usually but not exclusively cattle. They include milk, yogurt and cheese. Milk and its derivative products are a rich source of the mineral calcium, but also provide protein, phosphorus, vitamin A, and vitamin D. However, many dairy products are high in saturated fat and cholesterol compared to vegetables, fruits and whole grains, which is why skimmed products are available as an alternative. For adults, USDA recommends 3 cups of dairy products per day.

Meat is a major source of protein, as well as iron, zinc, and vitamin B12. Meats, poultry, and fish include beef, chicken, pork, salmon, tuna, and shrimp, eggs, spices and herbs are also in this group. However, since many of the same nutrients found in meat can also be found in foods like eggs, dry beans, and nuts, such foods are typically placed in the same category as meats, as meat alternatives. These include tofu, products that resemble meat or fish but are made with soy, eggs, and cheeses. The meat group is one of the major compacted food groups in the food guide pyramid. Although meats provide energy and nutrients, they are often high in fat and cholesterol, and can be high in sodium. Simply trimming off fatty tissue can go a long way towards reducing this negative effect. However, this tactic may prove to be ineffective, so large portions of meats are not recommended; 2-3 ounces per day of meat or alternatives are recommended. This is 3-5 servings. For those who don't consume meat or animal products (see Vegetarianism and Taboo food and drink), meat analogues, tofu, beans, lentils, chick peas, nuts and other high-in-protein vegetables make up this group.

Based on the above food groups, the FDA recommends that a healthy individual's daily diet should consist of approximately 2000 calories. This diet should include the following constituents, as illustrated in TABLE 1.

TABLE 1

Recommended Daily Intake Values.

| Constituent | Approximate Weight/Recommended Daily Intake (in grams) |
|---|---|
| Saturated Fat | 20 g |
| Trans Fat | No more than 1% of daily caloric intake |
| Cholesterol | 300 mg |
| Sodium | 2400 mg |
| Sugar | No more than 8% of daily caloric intake |
| Protein | 60 g |
| Dietary Fiber | 25 g |
| Potassium | 3500 mg |

Recommended Daily Intake ("RDI") is based on the daily dietary intake level of a nutrient which was considered (at the time they were defined) to be sufficient to meet the requirements of nearly all (97-98%) healthy individuals in each life-stage and gender group. The RDI is used to determine the Daily Value which is printed on food labels in the United States, Canada, and Australia.

Additionally, it is recommended that a healthy individual consume certain amount of vitamins and minerals, which are also calculated based on a specific RDI value, as shown in TABLE 2 below.

TABLE 2

Recommended Daily Intake Values for Vitamins/Minerals.

| Vitamin/Mineral | Recommended Daily Intake | Highest Recommended Dietary Allowance of Dietary Reference Intake |
|---|---|---|
| Vitamin A | 3000 IU | 10,000 IU |
| Vitamin C | 60 mg | 90 mg |
| Calcium | 1000 mg | 1300 mg |
| Iron | 18 mg | 18 mg |
| Vitamin D | 400 IU | 600 IU |
| Vitamin E | 30 IU | 15 mg (33 IU of synthetic) |
| Vitamin K | 80 µg | 120 µg |
| Thiamin | 1.5 mg | 1.2 mg |
| Riboflavin | 1.7 mg | 1.3 mg |
| Niacin | 20 mg | 16 mg |
| Vitamin B6 | 2 mg | 1.7 mg |
| Folate | 400 µg | 400 µg |
| Vitamin B12 | 6 µg | 2.4 µg |
| Biotin | 300 µg | 30 µg |
| Pantothenic acid | 10 mg | 5 mg |
| Phosphorus | 1000 mg | 1250 mg |
| Iodine | 150 µg | 150 µg |
| Magnesium | 400 mg | 420 mg |
| Zinc | 15 mg | 11 mg |
| Selenium | 70 µg | 55 µg |
| Copper | 2 mg | 900 µg |
| Manganese | 2 mg | 2.3 mg |
| Chromium | 120 µg | 35 µg |
| Molybdenum | 75 µg | 45 µg |
| Chloride | 3400 mg | 2300 mg |

As can be understood by one skilled in the art, the current subject matter's method is not limited to the listed constituents and vitamins/minerals in TABLE 1 and TABLE 2, respectively. As such, other constituents may be present in individual's diet and appropriate RDI values can be assigned to them. However, for ease of description, the current subject matter will be discussed in connection with the RDI values shown in TABLE 1.

The basis for this document is to define the technical and mathematical technique that is applied when calculating a specific consumer food product using the Food Facts Formula. This document structure will include tables, functions and mathematical examples to define the formula. The formula is used to define a specific score for a product from A to F. That way the consumer has a better perception of what they are feeding themselves and their family.

FIG. 1 illustrates an exemplary system for determining a nutritional value of a food item, according to some implementations of the current subject matter. The system 100 can include a platform engine 104 and a food database 106 communicatively coupled to the platform engine 104. The engine 104 can receive a query from a user 102 and determine a nutritional value for a particular food item that may be of interest to the user. The nutritional value can assist the user 102 in determination whether or not to consume a particular food item. A higher nutritional value can indicate that the food item can carry a positive health effect on the user's health, e.g., lower undesired cholesterol, improve blood circulation, improve brain functionalities, strengthen bone and/or muscle tissue(s), etc. A lower nutritional value can indicate that the food item may have negative health effects on the user's health, e.g., cause heartburn, increase undesired cholesterol, reduce blood circulation, increase user's weight, etc.

The platform engine 104 can be a software, a hardware and/or any combination thereof. The user 102 can access the platform engine 104 via a user interface (not shown in FIG. 1), e.g., a web interface. The user can use a personal computer, a laptop, a smartphone, a personal digital assistant ("PDA"), a cellular telephone, a tablet, and/or any other computing device that the user wishes to use. The platform engine 104 can be accessed wirelessly and/or via any wired network (e.g., an Internet, an intranet, a wide area network ("WAN"), a metropolitan area network ("MAN"), a wide area network ("WAN"), and/or any other network and/or any combination thereof).

The food database 106 can include information about different types of foods and/or food items. The food items can be distributed to consumers (e.g., individuals, stores, supermarkets, schools, corporations, educational institutions, hospitals, etc.), e.g., via retail, wholesale, in a restaurant, in a school, in a hospital, and/or in any other facility. The food items can be pre-packaged, raw, prepared, cooked, conserved, mixed together, and/or be available in any other fashion. The information that can be included in the database can include, but is not limited to, identification of a food item (e.g., name, etc.), type of the food item (e.g., meat, dairy, etc.), maker of the food item, as well as food item's number of calories, total/saturated/unsaturated fat values, potassium values, sodium values, sugar values, vitamin/mineral values, cholesterol values, carbohydrates values, fiber values, etc. The database 106 can be a structured database and can be located together with the platform engine 104 and/or separately. The platform engine 104 can further store results of the queries received from the user 102 in the database 106 and/or in any other database. The database 106 can also include values for controversial ingredients, which can be defined based on various regulations of government agencies in separate countries. An exemplary list of controversial ingredients can be found in Appendix A attached hereto.

In some implementations, the platform engine 104 can be used to determine nutritional value of a food item in at least one of the following categories: dairy products, eggs, spices and/or herbs, baby foods, fats and/or oils, coconut oil, poultry, sausages, luncheon meats, pork products, lamb, veal, finfish, shellfish and game, sauces and gravies, breakfast cereals, fruits and fruit juices, vegetables, vegetable products, beverages, baked products, sweets and snacks, cereal, grains and pasta, fast food, meals entrees and side dishes, ethnic foods, restaurant foods, nuts and seed products, supplements (protein shakes, meal replacements, sport drinks), and/or any other categories, and/or any combinations thereof.

In some implementations, the user 102 can issue a query (e.g., enter a particular product name) to the platform engine 104 via a user interface. Alternatively, the user 102 can select a particular category to which the food item bellows. The platform engine can then determine various values associated with the food item (e.g., number of calories, total/saturated/unsaturated fat values, potassium values, sodium values, sugar values, vitamin/mineral values, cholesterol values, carbohydrates values, fiber values, controversial ingredients, etc.) from the database 106. Based on the information obtained from the database 106, the engine 104 can determine the nutritional value for the food item. The platform engine 104 can also provide the user with various information that the user should be aware of (i.e., "things to know"). The "things to know" can be stored in the database 106 and/or in any other memory location and can include, but are not limited to, articles, books, governmental regulations, medical studies, etc. The "things to know" can also indicate to the user whether the food item of interest has high sugar value, high cholesterol value, good source of vitamins/minerals, etc. Some or all of this information can be displayed on a user interface and presented to the user on the user's computing system. Using this information, the user can determine whether or not to consume the food item.

Figure 2:
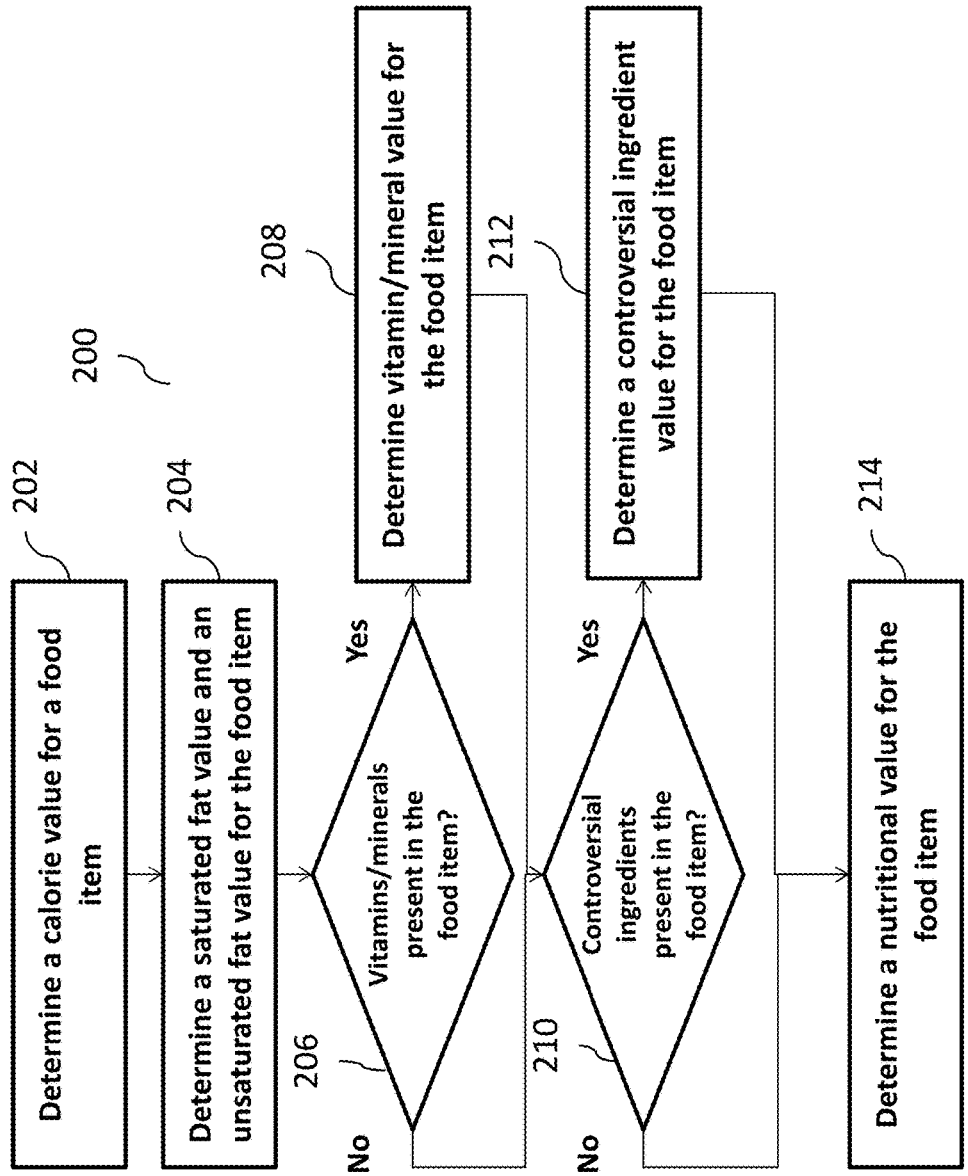
FIG. 2 illustrates an exemplary process that can be performed by the system shown in FIG. 1 to determine an overall nutritional value of a food item, according to some implementations of the current subject matter.

FIG. 2 illustrates an exemplary process 200 that can be performed by the system 100 to determine an overall nutritional value of a food item, according to some implementations of the current subject matter. At 202, upon receiving a query from the user 102 about a food item, the platform engine 104 can access the database 106 to obtain various values for the food item. The platform engine 104 can obtain a number of calories (in kilocalories) corresponding to the food item. Based on the obtained value and based on a category of food that the food item is in, the calorie value can be divided by a predetermined first factor corresponding to that category (exemplary factors are illustrated in the exemplary implementations discussed below).

At 204, the platform engine 104 accesses the database 106 to obtain values from the database 106 for saturated and/or unsaturated fats (and/or total fat) corresponding to the food item. The platform engine 104 obtains a corresponding predetermined factor (e.g., second factor, third factor, etc.) and divides the obtained value(s) by the corresponding predetermined factor(s). The factors can be selected based on a specific food category that the selected food item is in. Exemplary factors for the fats are illustrated in the exemplary implementations discussed below.

At 206, the platform engine 104 can determine from the database 106 whether any vitamins/minerals are present in the food item identified by the user 102. If vitamins/minerals are present, the platform engine 104 can determine a number of vitamins/minerals present and based on that number, can determine a factor to use to add to an overall nutritional value, at 208. If no vitamins/minerals are present, then no factors are added to the overall nutritional value and the process 200 can proceed to 210. Exemplary factors are illustrated in the exemplary implementations set forth below.

At 210, a number of controversial ingredients can be ascertained by the platform engine 104 using the database 106. Based on the number of ingredients, a controversial ingredient value for the food item can be ascertained, at 212. In some implementations, if any controversial ingredients (see, Appendix A for some exemplary controversial ingredients), the overall nutritional value is reduced by a factor 1.4, as illustrated in the exemplary implementations discussed below.

At 214, the platform engine 104 can determine the overall nutritional value of the food item by summing the values generated by the processing 200, at 202-212. In some implementations, values for potassium, sodium, sugar, cholesterol, carbohydrates, and fiber can be also obtained from the database 106 and can be used to affect the determination of the overall nutritional value of the food item, as illustrated below in connection with the exemplary implementations discussed below. In some implementations, the overall nutritional value of the food item can be determined based on food item's ingredients and/or constituents and nutritional facts (e.g., values, percentages, etc.) obtained from database 106 In some implementations, the database 106 can include a plurality of entries corresponding to various foods, their ingredients, values of ingredients, percentages, recommended daily values, information from the World Health Organization, Food and Drug Administration, U.S. Department of Agriculture, and/or any other agency and/or company, associated with a particular food item and/or ingredient, vitamin, mineral, etc., as well as any other attributes that may relate to food items and/or their constituents. The information can be entered and/or stored in any desired fashion (e.g., tables, text, numerical, etc.). Further, the ingredients can be listed in any desired way and/or order. For example, Hydrogenated Coconut Oil can be listed as "Coconut Oil Hydrogenated." The listing of information in a certain fashion can facilitate search for food items and/or their constituents. Further, the database 106 can be communicatively coupled to other database(s) that can contain information about allergens, effects of foods, etc. The database 106 can be communicatively coupled to database(s) of various governmental and/or commercial entities (e.g., World Health Organization, Food and Drug Administration, U.S. Department of Agriculture, etc.).

FIG. 3 illustrates exemplary tables 302 and 304 that illustrate values that can be stored at the database 106 and can be used to determine the overall nutritional value of the food item. Table 302 includes values and "letter grades" corresponding to contents of the food item, which can include number of calories, saturated/unsaturated fat, sodium, sugar, cholesterol, carbohydrates, and fiber. Each "letter grade" corresponds to a predetermine percentage of a particular component (e.g., calories, saturated/unsaturated fat, sodium, sugar, cholesterol, carbohydrates, and fiber) in the food item. For example, "letter grade A" corresponds to 0-20% of the total calories, 0-25% of the total carbohydrates, 0-10% saturated fat, 0-15% cholesterol, 0-20% sodium, and 0-30% unsaturated fat, 75-100% fiber, and less than 10% sugar. Depending of the determined percentage value of a specific component (e.g., calories, saturated/unsaturated fat, sodium, sugar, cholesterol, carbohydrates, and fiber) in the food item, the "letter grade" is determined and a corresponding value is obtained from table 304. The table 304 can also be stored in the database 106 and accessed by the platform engine 104. For example, "letter grade A" corresponds to a value of 4, as shown in FIG. 3.

Exemplary Implementations

The following is a discussion of some exemplary determination of nutritional values for some common food categories.

EXAMPLE 1

Dairy/Dairy Products

The following process can be implemented for determining a value of a dairy and/or dairy products (an exemplary numerical calculation 400 is illustrated in FIG. 4 (for America's Choice Grade A Whole Milk with Vitamin D (64 fl. oz)):

1. Divide the value for total calories (kcals) of the product by 330;
2. Divide the value for saturated fat of the product by 3.5 grams;
3. Divide the value for unsaturated fat of the product by 7.5 grams;
4. Divide the value of cholesterol of the product by 50 mg;
5. Divide the value of sodium of the product by 400 mg;
6. Divide the value of sugar of the product by 16 grams only if the ingredients list has added sugars. If naturally occurring sugars only exist, then ignore this step;
7. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points.
8. Obtain numerical value of the letter grade associated to each calculation used from Tables 302-304 shown in FIG. 3;
9. Add the values together and then divide by 6 if step 6 above was used or by 5 if step 6 was not used.
10. Subtract 1.4 if any controversial ingredient was found;
11. Based on the value left, obtain the letter grade from Tables 302-304 shown in FIG. 3.

EXAMPLE 2

Eggs

The following process can be implemented for determining a value of eggs:

1. Divide the value for total calories (kcals) of the product by 667;
2. Divide the value for saturated fat of the product by 7 grams;
3. Divide the value for unsaturated fat of the product by 15 grams;
4. Divide the value of sodium of the product by 200 mg;
5. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;

e. If 9+ vitamins and/or minerals are found, then award 5 bonus points.
6. Obtain numerical value of the letter grade associated with each calculation used from Tables 302-304 shown in FIG. 3;
7. Add values together and then divide by 4;
8. Subtract 1 if any controversial ingredients were found;
9. Based on the value left, obtain the letter grade from the table from Tables 302-304 shown in FIG. 3.

EXAMPLE 3

Spices and Herbs

The following process can be implemented for determining a value of spices and herbs:
1. Divide the value for total calories (kcals) of the product by 100;
2. Divide the value for saturated fat of the product by 1 gram;
3. Divide the value for unsaturated fat of the product by 2.5 grams;
4. Divide the value of cholesterol of the product by 16 mg;
5. Divide the value of sodium of the product by 130 mg;
6. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
7. Obtain numerical value of the letter grade associated to each calculation used from Tables 302-304 shown in FIG. 3;
8. Add values together and divide by 5;
9. Subtract 1.4 if any controversial ingredients were found;
10. Based on the value left, obtain the letter grade from Tables 302-304 shown in FIG. 3.

EXAMPLE 4

Baby Foods

The following process can be implemented for determining a value of baby foods:
1. Divide the value for total calories (kcals) of the product by 245;
2. Divide the value for total fat of the product by 10 grams;
3. Divide the value for carbohydrates of the product by 32 grams;
4. Divide the value of sodium of the product by 123 mg;
5. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
6. Obtain numerical value of the letter grade associated to each calculation used from Tables 302-304 shown in FIG. 3;
7. Add values together and then divide by 4;
8. Subtract 1.4 if any controversial ingredients were found;
9. Based on the value left, obtain the letter grade from Tables 302-304 shown in FIG. 3.

EXAMPLE 5

Fats and Oils

The following process can be implemented for determining a value of fats and oils:
1. Divide the value for saturated fat of the product by the value for total fat of the product;
2. Divide the value for unsaturated fat of the product by the value for total fat of the product;
3. Divide the value of cholesterol of the product by 100 mg;
4. Divide the value of sodium of the product by 800 mg;
5. Obtain numerical value of the letter grade associated to each calculation used from Tables 302-304 shown in FIG. 3;
5. Add values together and then divide by 4;
6. Subtract 1.4 if any controversial ingredients were found;
7. Based on the value left, obtain the letter grade from Tables 302-304 shown in FIG. 3.

EXAMPLE 6

Coconut Oil

The following process can be implemented for determining a value of coconut oil:
1. Multiple the value for saturated fat of the product by 35% and then divide by the value for total fat of the product;
2. Divide the value for unsaturated fat of the product by the value for total fat of the product;
3. Divide the value of cholesterol of the product by 100 mg;
4. Divide the value of sodium of the product by 800 mg;
5. Obtain numerical value of the letter grade associated to each calculation used from Tables 302-304 shown in FIG. 3;
6. Add values together and then divide by 4;
7. Subtract 1.4 if any controversial ingredients were found;
8. Based on the value left, obtain the letter grade from Tables 302-304 shown in FIG. 3.

EXAMPLE 7

Poultry, Sausages, Luncheon Meats, Pork Products, Lamb, Veal, Game, Finfish, and Shellfish The following process can be implemented for determining values of poultry, sausages, luncheon meats, pork products, lamb, veal, game, finfish, and shellfish:

1. Divide the value for total calories (kcals) of the product by 667;
2. Divide the value for saturated fat of the product by 7 grams;
3. Divide the value for unsaturated fat of the product by 15 grams;
4. Divide the value of cholesterol of the product by 100 mg;
5. Divide the value of sodium of the product by 400 mg;
6. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
7. Obtain numerical value of the letter grade associated to each calculation used from Tables 302-304 shown in FIG. 3;
8. Add values together and divide by 5;
9. Subtract 1.4 if any controversial ingredients were found;
10. Based on the value left, obtain the letter grade from Tables 302-304 shown in FIG. 3.

EXAMPLE 8

Sauces and Gravies

The following process can be implemented for determining values of sauces and gravies:
1. Divide the value for total calories (kcals) of the product by 222;
2. Divide the value for saturated fat of the product by 2.3 grams;
3. Divide the value for unsaturated fat of the product by 5 grams;
4. Divide the value of cholesterol of the product by 33 mg;
5. Divide the value of sodium of the product by 267 mg;
6. Divide the value of sugar of the product by 6 grams;
7. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
8. Obtain numerical value of the letter grade associated to each calculation used from Tables 302-304 shown in FIG. 3;
9. Add values together and divide by 6;
10. Subtract 1.4 if any controversial ingredients were found;
11. Based on the value left, obtain the letter grade from Tables 302-304 shown in FIG. 3.

EXAMPLE 9

Breakfast Cereals

Figure 5:
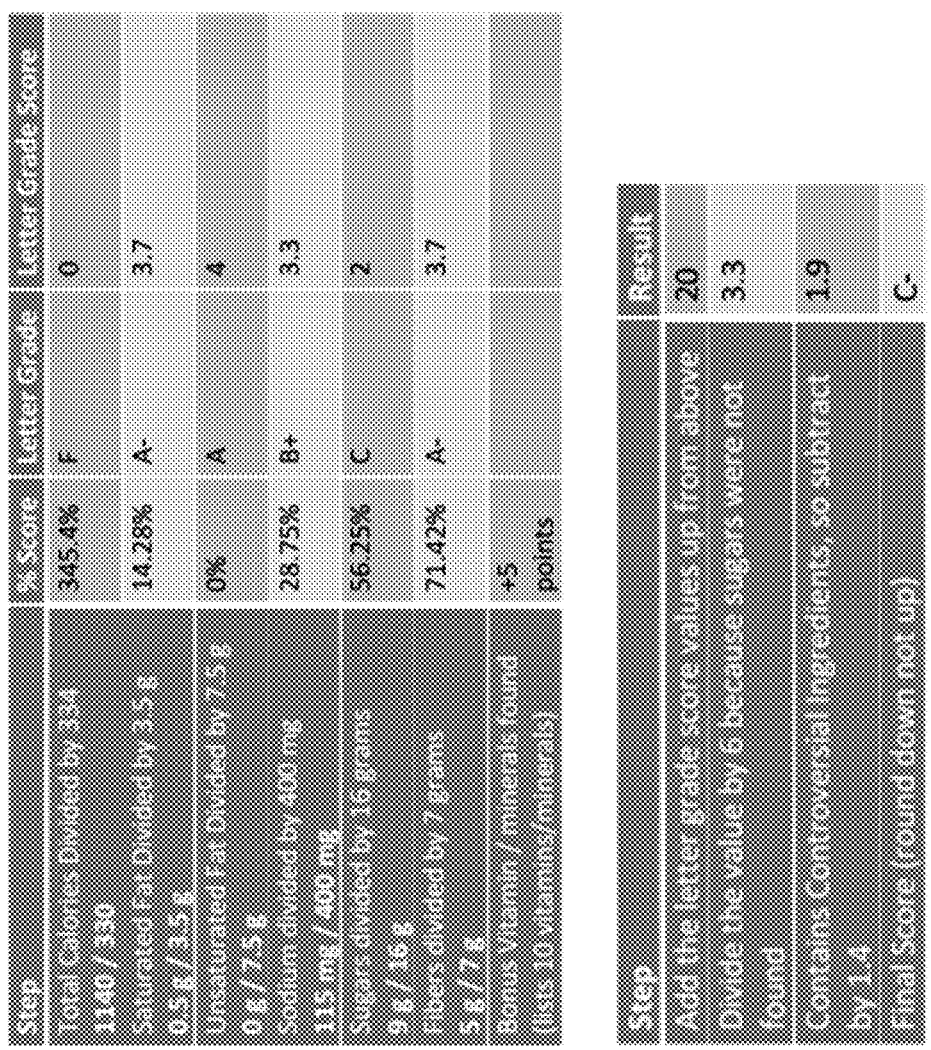
FIG. 5 illustrates another exemplary numerical calculation for a nutritional food item, according to some implementations of the current subject matter.

The following process can be implemented for determining values of breakfast cereals (an exemplary numerical calculation 500 is shown in FIG. 5 (for Special K Low Fat Touch of Honey Granola Cereal)):
1. Divide the value for total calories (kcals) of the product by 334;
2. Divide the value for saturated fat of the product by 3.5 grams;
3. Divide the value for unsaturated fat of the product by 7.5 grams;
4. Divide the value of sodium of the product by 400 mg;
5. Divide the value of sugar of the product by 6 grams;
6. Divide the value of fiber of the product by 7 grams;
7. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
8. Obtain numerical value of the letter grade associated to each calculation used from Tables 302-304 shown in FIG. 3;
9. Add values together and divide by 6;
10. Subtract 1.4 if any controversial ingredients were found;
11. Based on the value left, obtain the letter grade from Tables 302-304 shown in FIG. 3.

EXAMPLE 10

Fruits and Fruit Juices, Vegetables, and Vegetable Products

The following process can be implemented for determining values of fruits and fruit juices, vegetables, and vegetable products:
1. Divide the value for total calories (kcals) of the product by 667;
2. Divide the value for saturated fat of the product by 7 grams;
3. Divide the value for unsaturated fat of the product by 15 grams;
4. Divide the value of sodium of the product by 800 mg;
5. Divide the value of fiber of the product by 5 grams;
6. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;

d. If only 7 to 8 vitamins and/or minerals are found, then award 4 bonus points;
e. If 9+ vitamins and/or minerals are found, then award 5 bonus points;
7. Obtain numerical value of the letter grade associated to each calculation used from Tables 302-304 shown in FIG. 3;
8. Add values together and divide by 5;
9. Subtract 1.4 if any controversial ingredients were found;
10. Based on the value left, obtain the letter grade from Tables 302-304 shown in FIG. 3.

EXAMPLE 11

Beverages

The following process can be implemented for determining values of beverages:
1. Divide the value for total calories (kcals) of the product by 150;
2. Divide the value for sugar of the product by 25 grams;
3. Divide the value of sodium of the product by 400 mg;
4. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
5. Obtain numerical value of the letter grade associated to each calculation used from Tables 302-304 shown in FIG. 3;
6. Add values together and divide by 3;
7. Subtract 1.4 if any controversial ingredients were found;
8. Based on the value left, obtain the letter grade from Tables 302-304 shown in FIG. 3.

EXAMPLE 12

Baked Products, Sweets, and Snacks

The following process can be implemented for determining values of baked products, sweets, and snacks:
1. Divide the value for total calories (kcals) of the product by 300.
2. Divide the value for saturated fat of the product by 3 grams;
3. Divide the value of unsaturated fat of the product by 7 grams;
4. Divide the value of cholesterol of the product by 45 mg;
5. Divide the value of sodium of the product by 36
6. Divide the value of sugar of the product by 16 grams only if in the ingredients list added sugars are found. If naturally occurring sugars only exist then ignore this step;
7. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
8. Obtain the numerical value of the letter grade associated to each calculation used from Tables 302-304 shown in FIG. 3;
9. Add values together and divide by 6 if step 6 was used or by 5 if step 6 was not used;
10. Subtract 1.4 if any controversial ingredients were found;
11. Based on the value left, obtain the letter grade from Tables 302-304 shown in FIG. 3.

EXAMPLE 13

Cereal, Grains and Pasta

The following process can be implemented for determining values of cereal, grains and pasta:
1. Divide the value for total calories (kcals) of the product by 667;
2. Divide the value for saturated fat of the product by 7 grams;
3. Divide the value of unsaturated fat of the product by 15 grams;
4. Divide the value of sodium of the product by 800 mg;
5. Divide the value of fiber of the product by 8 grams;
6. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
7. Obtain numerical value of the letter grade associated to each calculation used from Tables 302-304 shown in FIG. 3;
8. Add values together and divide by 5;
9. Subtract 1.4 if any controversial ingredients were found;
10. Based on the value left, obtain the letter grade from Tables 302-304 shown in FIG. 3.

EXAMPLE 14

Fast Food, Meals, Entrees and Side Dishes, Ethnic Foods, Restaurant Foods

The following process can be implemented for determining values of fast food, meals, entrees and side dishes, ethnic foods, restaurant foods:
1. Divide the value for total calories (kcals) of the product by 667;

2. Divide the value for saturated fat of the product by 7 grams;
3. Divide the value of unsaturated fat of the product by 15 grams;
4. Divide the value of cholesterol of the product by 100 mg;
5. Divide the value of sodium of the product by 800 mg;
6. Divide the value of fiber of the product by 8 grams;
6. Divide the value of sugar of the product by 16 grams;
7. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
8. Obtain numerical value of the letter grade associated to each calculation used from Tables 302-304 shown in FIG. 3;
9. Add values together and divide by 7;
10. Subtract 1.4 if any controversial ingredients were found;
11. Based on the value left, obtain the letter grade from Tables 302-304 shown in FIG. 3.

EXAMPLE 14

Nut and Seed Products

The following process can be implemented for determining values of nut and seed products:
1. Divide the value for total calories (kcals) of the product by 667;
2. Divide the value for saturated fat of the product by the value for the total fat of the product;
3. Divide the value of unsaturated fat of the product by the value for the total fat of the product;
4. Divide the value of cholesterol of the product by 100 mg;
5. Divide the value of sodium of the product by 100 mg;
6. Divide the value of fiber of the product by 7 grams;
7. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
8. Obtain numerical value of the letter grade associated to each calculation used from Tables 302-304 shown in FIG. 3;
9. Add values together and divide by 6;
10. Subtract 1.4 if any controversial ingredients were found;
11. Based on the value left, obtain the letter grade from Tables 302-304 shown in FIG. 3.

EXAMPLE 15

Supplements (Protein Shakes, Meal Replacements, Sports Drinks)

The following process can be implemented for determining values of supplements (protein
1. Divide the value for total calories (kcals) of the product by 400;
2. Divide the value for saturated fat of the product by 4 grams;
3. Divide the value of unsaturated fat of the product by 9 grams;
4. Divide the value of fiber of the product by 5 grams;
5. Divide the value of sodium of the product by 400 mg;
6. Add bonus points if there are any vitamins and/or minerals existing in the nutrition facts of the product. Bonus points can be determined as follows:
   a. If only 1 to 2 vitamins and/or minerals are found, then award 1 bonus point;
   b. If only 3 to 4 vitamins and/or minerals are found, then award 2 bonus points;
   c. If only 5 to 6 vitamins and/or minerals are found, then award 3 bonus points;
   d. If only 7 to 8 vitamins and/or minerals are found, then award 4 bonus points;
   e. If 9+ vitamins and/or minerals are found, then award 5 bonus points;
7. Obtain numerical value of the letter grade associated to each calculation used from Tables 302-304 shown in FIG. 3;
8. Add values together and divide by 4 if in step 4 if fiber was found to be present, otherwise divide by 5 if fiber was found to be present in step 4;
9. Subtract 1.4 if any controversial ingredients were found;
10. Based on the value left, obtain the letter grade from Tables 302-304 shown in FIG. 3.

Figure 6:
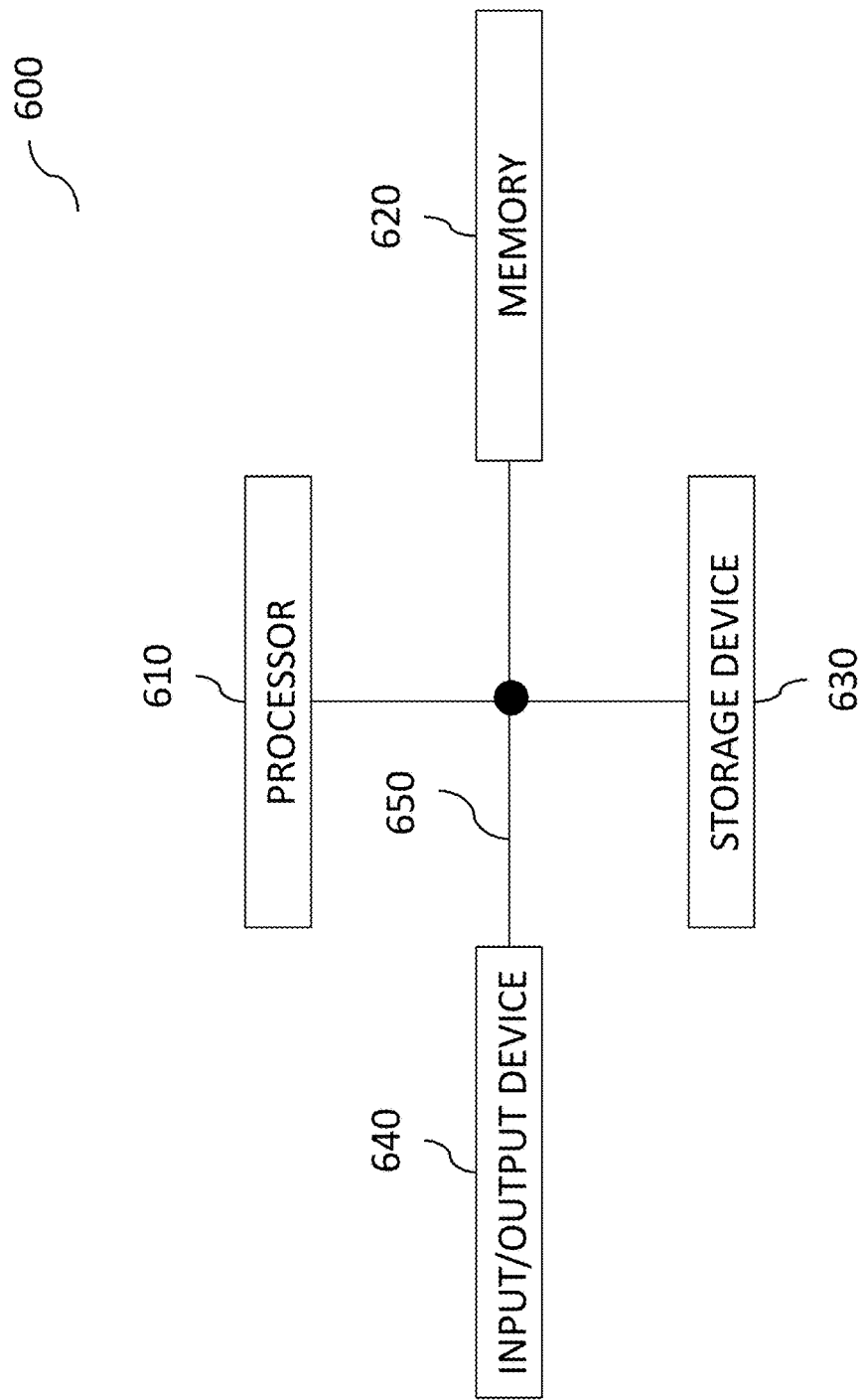
FIG. 6 is an exemplary system, according to some implementations of the current subject matter.

In some implementations, the current subject matter can be configured to be implemented in a system 600, as shown in FIG. 6. The system 600 can include a processor 610, a memory 620, a storage device 630, and an input/output device 640. Each of the components 610, 620, 630 and 640 can be interconnected using a system bus 650. The processor 610 can be configured to process instructions for execution within the system 600. In some implementations, the processor 610 can be a single-threaded processor. In alternate implementations, the processor 610 can be a multi-threaded processor. The processor 610 can be further configured to process instructions stored in the memory 620 or on the storage device 630, including receiving or sending information through the input/output device 640. The memory 620 can store information within the system 600. In some implementations, the memory 620 can be a computer-readable medium. In alternate implementations, the memory 620 can be a volatile memory unit. In yet some implementations, the memory 620 can be a non-volatile memory unit. The storage device 630 can be capable of providing mass storage for the system 600. In some implementations, the storage device 630 can be a computer-readable medium. In alternate implementations, the storage device 630 can be a floppy disk device, a hard disk device, an optical disk device, a tape device, non-volatile solid state memory, or any other type of storage device. The input/output device

640 can be configured to provide input/output operations for the system 600. In some implementations, the input/output device 640 can include a keyboard and/or pointing device. In alternate implementations, the input/output device 640 can include a display unit for displaying graphical user interfaces.

Figure 7:
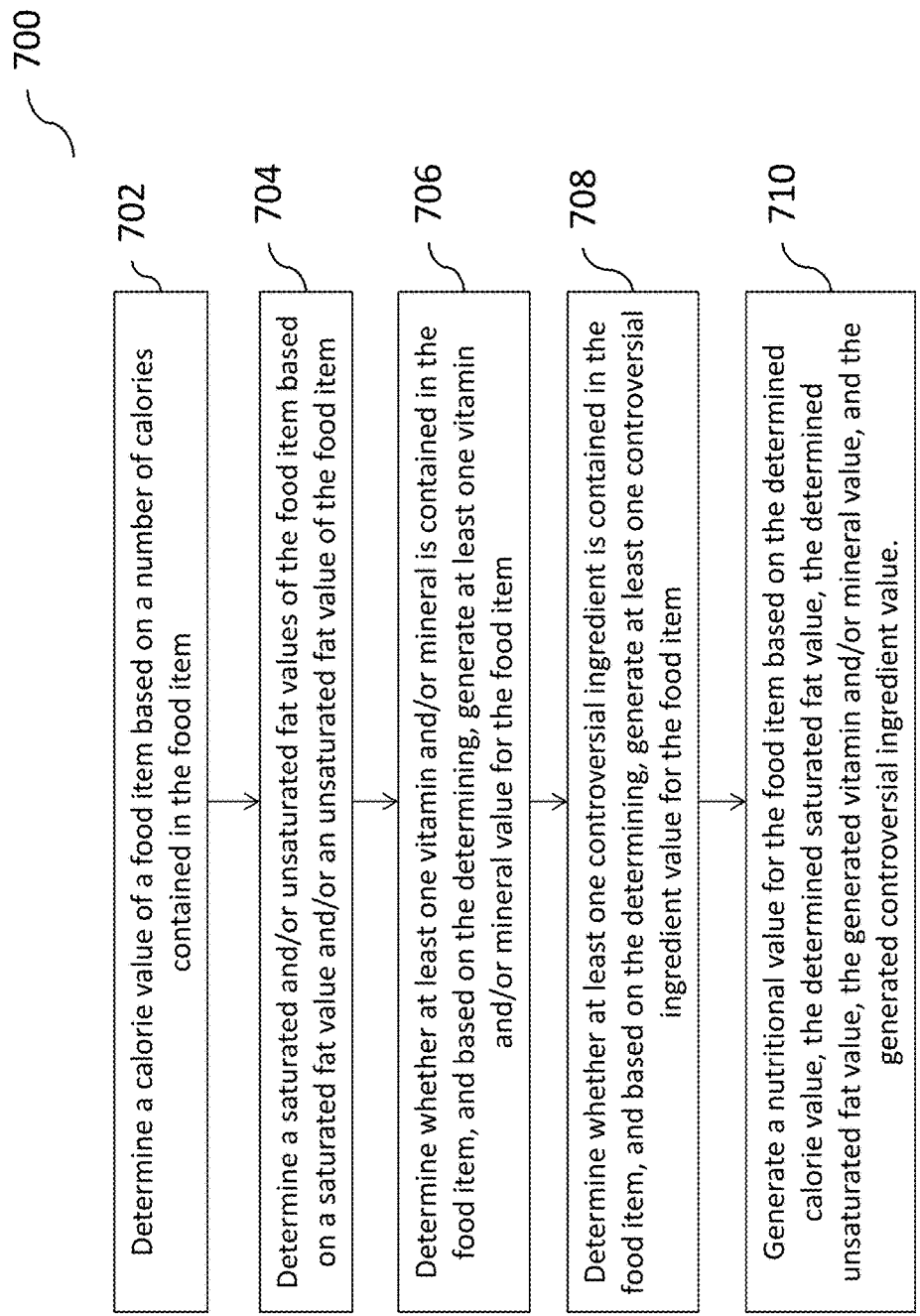
FIG. 7 is an exemplary method, according to some implementations of the current subject matter.

FIG. 7 illustrates an exemplary method 700 for determining a nutritional value of a food item, according to some implementations of the current subject matter. At 702, in response to a query from a user, a calorie value of a food item can be determined based on a number of calories contained in the food item using at least one processor coupled to at least one database (e.g., the platform engine 104 and the database 106 shown in FIG. 1). At 704, saturated and/or unsaturated fat values of the food item can be determined based on a saturated fat value and/or an unsaturated fat value of the food item. At 706, a determination can be made whether at least one vitamin and/or mineral is contained in the food item. Based on that determination, at least one vitamin and/or mineral value for the food item can be generated. At 708, a determination can be made whether at least one controversial ingredient is contained in the food item. Based on that determination at least one controversial ingredient value for the food item can be generated. At 710, a nutritional value for the food item based on the determined calorie value, the determined saturated fat value, the determined unsaturated fat value, the generated vitamin and/or mineral value, and the generated controversial ingredient value can be generated.

In some implementations, the current subject matter can include at least one of the following optional features. The nutritional value of the food item can be determined based on a 2000-calorie diet for the user. In some implementations, the diet can be based on a higher and/or smaller number of calories. For example, U.S. Department of Agriculture recommends a lower calorie diet for certain individuals, such as, very young children, whose diet can be at least partially based on baby food and/or baby formula. The calorie value can be determined based on a total number of calories contained in the food item and at least one first factor corresponding to a category of food that includes the food item. The saturated and/or unsaturated fat values can be determined based on a total percentage of saturated and/or unsaturated fats contained in the food item and at least one second factor corresponding to a category of food that includes the food item. The vitamins/minerals values can be determined based on a total percentage of vitamins/minerals contained in the food item and at least one third factor corresponding to a category of food that includes the food item. The controversial ingredients values can be determined based on a number of controversial ingredients contained in the food item and at least one fourth factor corresponding to a category of food that includes the food item. The fourth factor can be a constant.

In some implementations, the method can include determining a value of at least one of the following: a potassium value, a sodium value, a sugar value, a cholesterol value, a carbohydrates value, and a fiber value of the food item. The generated nutritional value can be generated based on at least one of the following: the determined potassium value, sodium value, sugar value, cholesterol value, carbohydrates value, and fiber value of the food item.

The systems and methods disclosed herein can be embodied in various forms including, for example, a data processor, such as a computer that also includes a database, digital electronic circuitry, firmware, software, or in combinations of them. Moreover, the above-noted features and other aspects and principles of the present disclosed implementations can be implemented in various environments. Such environments and related applications can be specially constructed for performing the various processes and operations according to the disclosed implementations or they can include a general-purpose computer or computing platform selectively activated or reconfigured by code to provide the necessary functionality. The processes disclosed herein are not inherently related to any particular computer, network, architecture, environment, or other apparatus, and can be implemented by a suitable combination of hardware, software, and/or firmware. For example, various general-purpose machines can be used with programs written in accordance with teachings of the disclosed implementations, or it can be more convenient to construct a specialized apparatus or system to perform the required methods and techniques.

The systems and methods disclosed herein can be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

As used herein, the term "user" can refer to any entity including a person or a computer.

Although ordinal numbers such as first, second, and the like can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the invention, which is defined by the scope of the appended claims. Other implementations are within the scope of the following claims.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user can provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input.

The subject matter described herein can be implemented in a computing system that includes a back-end component, such as for example one or more data servers, or that includes a middleware component, such as for example one or more application servers, or that includes a front-end component, such as for example one or more client computers having a graphical user interface or a Web browser through which a user can interact with an implementation of the subject matter described herein, or any combination of such back-end, middleware, or front-end components. The components of the system can be interconnected by any form or medium of digital data communication, such as for example a communication network. Examples of communication networks include, but are not limited to, a local area network ("LAN"), a wide area network ("WAN"), and the Internet.

The computing system can include clients and servers. A client and server are generally, but not exclusively, remote from each other and typically interact through a communication network. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations can be within the scope of the following claims.

APPENDIX A

Exemplary listing of controversial ingredients:
Acesulfame Potassium
Alum
Aspartame
Azodicarbonamide
Barley Malt Flour
Barley Malted Flour
Benzoic Acid
BHA
BHT
Blue 1
Blue 1 Lake
Blue 2
Blue 2 Lake
Butylated Hydroxytoluene BHT
Caffeine
Calcium Caseinate
Canola Oil Hydrogenated
Canola Oil Partially Hydrogenated
Canola Oil Shortening Partially Hydrogenated
Canola Partially Hydrogenated
Caramel Color
Carmine
Carrageenan
Carrageenan Gum
Casein Hydrolyzed
Cherries Artificially Colored Red
Chicken Fat
Cochineal Extract
Coconut Oil Hydrogenated
Coconut Oil Partially Hydrogenated
Coconut Partially Hydrogenated
Coloring
Coloring Natural
Colors Added
Colors Artificial
Colors Artificial
Colors Natural & Artificial
Corn Gluten Hydrolyzed
Corn Gluten Protein Hydrolyzed
Corn Hydrolyzed
Corn Maltodextrin
Corn Oil Hydrogenated
Corn Oil Partially Hydrogenated
Corn Protein Hydrolyzed
Corn Syrup High Fructose
Corn Syrup Solids
Cottonseed Oil Hydrogenated
Cottonseed Oil Partially Hydrogenated
Cottonseed Oil Partially Hydrogenated and Modified
Cottonseed Oil Partially Hydrolyzed
Cottonseed Oil Shortening Hydrogenated
Cottonseed Partially Hydrogenated
Cottonseed Shortening Partially Hydrogenated
Diacetyl
Diacetyl Tartaric Acid Esters of Fatty Acids
Disodium 5' Guanylate
Disodium EDTA
Disodium Guanylate
Disodium Inosinate
Eggs Hydrolyzed
Ethoxyquin
Flavored Chips Caramel
Flavored Chips Peanut Butter
Flavored Coating Chocolate
Flavored Coating Chocolate Milk
Flavored Coating Peanut
Flavored Filling Cheesecake
Flavored Filling Mozzarella Cheese
Flavored Fruit Pieces Blueberry
Flavored Fruit Pieces Cherry
Flavored Fruit Pieces Raspberry
Flavored Naturally Smoke Provolone Cheese
Flavored Oil Butter Flavoring Artificial and Natural
Flavoring Beef
Flavoring Extractive Spice
Flavoring Malt
Flavoring Natural
Flavoring Natural Malt
Flavoring Natural Mint
Flavors
Flavors Almonds
Flavors and Color Artificial
Flavors and Color Natural
Flavors Apple
Flavors Artificial
Flavors Artificial Avocado
Flavors Artificial Banana
Flavors Artificial Blueberry
Flavors Artificial Blueberry Bits
Flavors Artificial Butter
Flavors Artificial Caramel
Flavors Artificial Cheese
Flavors Artificial Maple
Flavors Artificial Peach
Flavors Artificial Strawberry
Flavors Artificial Vanilla
Flavors Artificial Vanillin
Flavors Bacon
Flavors Base Beef
Flavors Base Parmesan Cheese
Flavors Base Roasted Garlic
Flavors Bits
Flavors Blend Brown Sugar
Flavors Blend Chocolate
Flavors Blend Vegetable
Flavors Broth Vegetable
Flavors Burgundy Wine
Flavors Butter
Flavors Buttermilk
Flavors Cheddar Cheese
Flavors Cheese
Flavors Chicken
Flavors Citrus
Flavors Cola
Flavors Cookie Dough
Flavors Crab
Flavors Cream
Flavors Enhancer
Flavors Garlic
Flavors Ginger
Flavors Grass Lemon
Flavors Grill
Flavors Grilled Chicken
Flavors Hickory
Flavors Imitation
Flavors Jasmine
Flavors Liquid Smoke Mesquite
Flavors Mandarin Oranges
Flavors Mushroom
Flavors Natural
Flavors Natural & Artificial
Flavors Natural & Artificial Apple
Flavors Natural & Artificial Berry
Flavors Natural & Artificial Blueberry
Flavors Natural & Artificial Blueberry Bits
Flavors Natural & Artificial Butter
Flavors Natural & Artificial Honey
Flavors Natural & Artificial Raspberry
Flavors Natural & Artificial Strawberry
Flavors Natural & Artificial Vanilla
Flavors Natural Acerola
Flavors Natural and Artificial Cherry
Flavors Natural and Artificial Oranges
Flavors Natural and Artificial Peanut
Flavors Natural Apple
Flavors Natural Bacon
Flavors Natural Bananas
Flavors Natural Blackberry
Flavors Natural Blueberry
Flavors Natural Butter
Flavors Natural Cheddar Cheese
Flavors Natural Cheese
Flavors Natural Cherry
Flavors Natural Chicken
Flavors Natural Citrus
Flavors Natural Citrus
Flavors Natural Grape
Flavors Natural Grill
Flavors Natural Honey
Flavors Natural Kiwi & Strawberry
Flavors Natural Lemon and Lime
Flavors Natural Lemons
Flavors Natural Lime
Flavors Natural Mango
Flavors Natural Mangosteen
Flavors Natural Maple
Flavors Natural Manila
Flavors Natural Nutmeg
Flavors Natural Oranges
Flavors Natural Passionfruit
Flavors Natural Peaches
Flavors Natural Peanut
Flavors Natural Pineapple
Flavors Natural Plums
Flavors Natural Pork
Flavors Natural Prickly Pear Cactus
Flavors Natural Raspberry
Flavors Natural Smoke
Flavors Natural Smoke Hickory
Flavors Natural Smoke Mesquite
Flavors Natural Spice
Flavors Natural Strawberry
Flavors Natural Tomatoes
Flavors Natural Vanilla
Flavors Natural Wasabi
Flavors Natural Yuza
Flavors Onions
Flavors Oranges
Flavors Packet
Flavors Peanuts
Flavors Pork
Flavors Potatoes
Flavors Roast Chicken
Flavors Root Beer
Flavors Roux Gravy Turkey
Flavors Sarsaparilla
Flavors Sherry
Flavors Shrimp
Flavors Smoke
Flavors Smoke Hickory
Flavors Smoke Imitation Turkey
Flavors Smoke Mesquite
Flavors Smoked Pork
Flavors Sour Cream
Flavors Syrup Chocolate
Flavors Tortilla Flavors Turkey
Flavors Type Beef
Flavors Type Bourbon
Flavors Type Chicken
Flavors Type Gravy Turkey
Flavors Vanilla
Flavors Vanillin
Flavors Wine Madeira
Flavors with Other Naturally Flavors Cherry
Gelatin
Gelatin Hydrolyzed
Glucose Syrup Hydrogenated
Gluten Protein Hydrolyzed
Green 3
Hydrolyzed
Mineral Oil
Monosodium Glutamate
Nickelous Sulfate
Olestra
Palm Hydrogenated
Palm Kernel Oil Hydrogenated
Palm Kernel Oil Partially Hydrogenated
Palm Kernel Partially Hydrogenated
Palm Oil Fractionated Partially Hydrogenated
Palm Oil Hydrogenated
Palm Oil Partially Hydrogenated
Palm Oil Partially Hydrogenated Modified
Palm Olein
Palm Shortening Partially Hydrogenated
Paprika with Extractives of Natural Flavors
Phosphoric Acid
Plant Protein Hydrolyzed
Polyethylene Glycol
Polysorbate 60
Polysorbate 65
Polysorbate 80
Potassium Benzoate
Potassium Bromate
Potassium Propionate
Propyl Gallate
Propylene Glycol
Protein Hydrolyzed
Rapeseed Oil Fractionated Partially Hydrogenated
Rapeseed Oil Fully Hydrogenated
Rapeseed Oil Hydrogenated
Rapeseed Oil Partially Hydrogenated
Red 3
Red 40
Red 40 Lake
Salatrim
Sodium Benzoate
Sodium Bisulfite
Sodium Caseinate
Sodium Lauryl Sulfate
Sodium Nitrate Nitrite
Sorbitol
Soy and Corn Protein Hydrolyzed
Soy Gluten Protein Hydrolyzed
Soy Hydrolyzed
Soy Oil Partially hydrogenated
Soy Protein Hydrogenated
Soy Protein Hydrolyzed
Soy Sauce
Soy Sauce Decolorized
Soy Sauce Naturally Brewed
Soy Sauce Powder
Soy Sauce Solids
Soya Protein Hydrolyzed
Soybeans Oil Brominated
Soybeans Oil Fried in Partially Hydrogenated
Soybeans Oil Fully Hydrogenated
Soybeans Oil Hydrogenated
Soybeans Oil Partially Hydrogenated
Soybeans Oil Partially Hydrogenated and Modified
Soybeans Oil Partially Hydrolyzed
Soybeans Oil with BHT Partially Hydrogenated
Soybeans Oil with Propylene Glycol Partially Hydrogenated
Soybeans Oil With Soy Lecithin Partially Hydrogenated
Soybeans Partially Hydrogenated
Soybeans Protein Hydrolyzed
Soybeans Shortening Partially Hydrogenated
Starch Hydrolysate Hydrogenated
Sulfer Dioxide
Sulpher Sulfur Dioxide
Sunflower Oil Partially Hydrogenated
TBHQ
Torula Protein Hydrolyzed
Tumeric Oleoresin
Turmeric Oleoresin
Vegetables Fat Hydrogenated
Vegetables Oil Brominated
Vegetables Oil Fried in Partially Hydrogenated
Vegetables Oil Hydrogenated
Vegetables Oil Partially Hydrogenated
Vegetables Oil Shortening Partially Hydrogenated
Vegetables Oils Fully Hydrogenated
Vegetables Protein Hydrolyzed
Vegetables Shortening Hydrogenated
Vegetables Shortening Partially Hydrogenated
Wheat Gluten Hydrolyzed
Wheat Gluten Protein Hydrolyzed
Wheat Protein Hydrolyzed
Whey Protein Hydrolyzed
Whey Protein Partially Hydrolyzed
Yeast Autolyzed
Yeast Autolyzed Extract With Natural Flavors
Yeast Brewer's Hydrolyzed
Yeast Extract
Yeast Extract Autolyzed
Yeast Extract Autolyzed Dried
Yeast Food
Yeast Hydrolyzed
Yeast Protein Brewers Hydrolyzed
Yeast Protein Hydrolyzed
Yeast Torula Hydrolyzed
Yeast Torula Protein Hydrolyzed
Yellow 5
Yellow 5 Lake
Yellow 6
Yellow 6 Lake

What is claimed:
1. A computer-implemented method, comprising:
determining, in response to a query from a user, using at least one processor coupled to at least one first database, a calorie value of a food item based on a number of calories contained in the food item, the query including at least one query parameter and being received from a graphical user interface communicatively coupled to the at least one processor using a first communication link, the at least one processor submitting the received query to the at least one first database;

executing, based on the at least one query parameter, a search query of the at least one first database to determine the number of calories contained in the food item,
wherein a processor associated with the at least one first database
communicating with at least one second database communicatively coupled to the at least one first database, the at least one second database including at least one government database and at least one third party database;
executing a query of the at least one second database to obtain information associated with the food item; and
providing the obtained information to the processor associated with the first database; and
determining a food category corresponding to the food item;
selecting, based on the determined category of the food item, a first factor in the plurality of factors corresponding to the determined food category;
generating, based on the executed search and analysis of the obtained information, the calorie value of the food item, the generating including applying the first factor to generate the calorie value of the food item;
determining, using the at least one processor coupled to the at least one first database, a saturated and/or unsaturated fat values of the food item based on a saturated fat value and/or an unsaturated fat value of the food item, wherein the saturated fat value and/or the unsaturated fat value are generated based on the executed search query of the at least one first database and analysis of the information obtained from the at least one second database, the determining the saturated and/or unsaturated fat values including selecting, based on the determined category of the food item, a second factor, being different from the first factor, in the plurality of factors corresponding to the determined food category, and applying the second factor to determine the saturated and/or unsaturated fat values;
generating, using the at least one processor, at least one vitamin and/or mineral value for the food item based on the executed search query of the at least one first database and analysis of the information obtained from the at least one second database, the generating the at least one vitamin and/or mineral values including selecting, based on the determined category of the food item, a third factor, being different from the first and second factors, in the plurality of factors corresponding to the determined food category, and applying the third factor to determine the at least one vitamin and/or mineral values;
generating, using the at least one processor, at least one controversial ingredient value for the food item based on the executed search query of the at least one first database and analysis of the information obtained from the at least one second database; and
generating, using the at least one processor, a nutritional value for the food item based on a combination of the determined calorie value, the determined saturated fat value, the determined unsaturated fat value, the generated vitamin and/or mineral value, and the generated controversial ingredient value, and arranging the generated nutritional value for the food item for display on the graphical user interface.

2. The method according to claim 1, wherein the nutritional value of the food item is determined based on a 2000-calorie diet for the user.

3. The method according to claim 1, wherein the calorie value is determined based on a total number of calories contained in the food item and at least one first factor corresponding to a category of food that includes the food item.

4. The method according to claim 1, wherein the saturated and/or unsaturated fat values are determined based on a total percentage of saturated and/or unsaturated fats contained in the food item and at least one second factor corresponding to a category of food that includes the food item.

5. The method according to claim 1, wherein the vitamins/minerals values are determined based on a total percentage of vitamins/minerals contained in the food item and at least one third factor corresponding to a category of food that includes the food item.

6. The method according to claim 1, wherein the controversial ingredients values are determined based on a number of controversial ingredients contained in the food item and at least one fourth factor corresponding to a category of food that includes the food item.

7. The method according to claim 6, wherein the fourth factor is a constant.

8. The method according to claim 1, further comprising determining a value of at least one of the following: a potassium value, a sodium value, a sugar value, a cholesterol value, a carbohydrates value, and a fiber value of the food item;
wherein the generated nutritional value is generated based on at least one of the following: the determined potassium value, sodium value, sugar value, cholesterol value, carbohydrates value, and fiber value of the food item.

9. A system comprising:
at least one programmable processor; and
a machine-readable medium storing instructions that, when executed by the at least one programmable processor, cause the at least one programmable processor to perform operations comprising:
determining, in response to a query from a user, using at least one processor coupled to at least one first database, a calorie value of a food item based on a number of calories contained in the food item, the query including at least one query parameter and being received from a graphical user interface communicatively coupled to the at least one processor using a first communication link, the at least one processor
submitting the received query to the at least one first database;
executing, based on the at least one query parameter, a search query of the at least one first database to determine the number of calories contained in the food item,
wherein a processor associated with the at least one first database
communicating with at least one second database communicatively coupled to the at least one first database, the at least one second database including at least one government database and at least one third party database;
executing a query of the at least one second database to obtain information associated with the food item; and providing the obtained information to the processor associated with the first database; and
determining a food category corresponding to the food item;
selecting, based on the determined category of the food item, a first factor in the plurality of factors corresponding to the determined food category;
generating, based on the executed search and analysis of the obtained information, the calorie value of the food item, the generating including applying the first factor to generate the calorie value of the food item;
determining, using the at least one processor coupled to the at least one first database, a saturated and/or unsaturated fat values of the food item based on a saturated fat value and/or an unsaturated fat value of the food item, wherein the saturated fat value and/or the unsaturated fat value are generated based on the executed search query of the at least one first database and analysis of the information obtained from the at least one second database, the determining the saturated and/or unsaturated fat values including selecting, based on the determined category of the food item, a second factor, being different from the first factor, in the plurality of factors corresponding to the determined food category, and applying the second factor to determine the saturated and/or unsaturated fat values;
generating, using the at least one processor, at least one vitamin and/or mineral value for the food item based on the executed search query of the at least one first database and analysis of the information obtained from the at least one second database, the generating the at least one vitamin and/or mineral values including selecting, based on the determined category of the food item, a third factor, being different from the first and second factors, in the plurality of factors corresponding to the determined food category, and applying the third factor to determine the at least one vitamin and/or mineral values;
generating, using the at least one processor, at least one controversial ingredient value for the food item based on the executed search query of the at least one first database and analysis of the information obtained from the at least one second database; and
generating, using the at least one processor, a nutritional value for the food item based on a combination of the determined calorie value, the determined saturated fat value, the determined unsaturated fat value, the generated vitamin and/or mineral value, and the generated controversial ingredient value, and arranging the generated nutritional value for the food item for display on the graphical user interface.

10. The system according to claim 9, wherein the nutritional value of the food item is determined based on a 2000-calorie diet for the user.

11. The system according to claim 9, wherein the calorie value is determined based on a total number of calories contained in the food item and at least one first factor corresponding to a category of food that includes the food item.

12. The system according to claim 9, wherein the saturated and/or unsaturated fat values are determined based on a total percentage of saturated and/or unsaturated fats contained in the food item and at least one second factor corresponding to a category of food that includes the food item.

13. The system according to claim 9, wherein the vitamins/minerals values are determined based on a total percentage of vitamins/minerals contained in the food item and at least one third factor corresponding to a category of food that includes the food item.

14. The system according to claim 9, wherein the controversial ingredients values are determined based on a number of controversial ingredients contained in the food item and at least one fourth factor corresponding to a category of food that includes the food item.

15. The system according to claim 14, wherein the fourth factor is a constant.

16. The system according to claim 9, wherein the operations further comprise
determining a value of at least one of the following: a potassium value, a sodium value, a sugar value, a cholesterol value, a carbohydrates value, and a fiber value of the food item;
wherein the generated nutritional value is generated based on at least one of the following: the determined potassium value, sodium value, sugar value, cholesterol value, carbohydrates value, and fiber value of the food item.

17. A computer program product comprising a non-transitory machine-readable medium storing instructions that, when executed by at least one programmable processor, cause the at least one programmable processor to perform operations comprising:
determining, in response to a query from a user, using at least one processor coupled to at least one first database, a calorie value of a food item based on a number of calories contained in the food item, the query including at least one query parameter and being received from a graphical user interface communicatively coupled to the at least one processor using a first communication link, the at least one processor
submitting the received query to the at least one first database;
executing, based on the at least one query parameter, a search query of the at least one first database to determine the number of calories contained in the food item,
wherein a processor associated with the at least one first database
communicating with at least one second database communicatively coupled to the at least one first database, the at least one second database including at least one government database and at least one third party database;
executing a query of the at least one second database to obtain information associated with the food item; and
providing the obtained information to the processor associated with the first database; and
determining a food category corresponding to the food item;
selecting, based on the determined category of the food item, a first factor in the plurality of factors corresponding to the determined food category;
generating, based on the executed search and analysis of the obtained information, the calorie value of the food item, the generating including applying the first factor to generate the calorie value of the food item;
determining, using the at least one processor coupled to the at least one first database, a saturated and/or unsaturated fat values of the food item based on a saturated fat value and/or an unsaturated fat value of the food item, wherein the saturated fat value and/or the unsaturated fat value are generated based on the executed search query of the at least one first database and analysis of the information obtained from the at least one second database, the determining the saturated and/or unsaturated fat values including selecting, based on the determined category of the food item, a second factor, being different from the first factor, in the plurality of factors corresponding to the determined food category, and applying the second factor to determine the saturated and/or unsaturated fat values;

generating, using the at least one processor, at least one vitamin and/or mineral value for the food item based on the executed search query of the at least one first database and analysis of the information obtained from the at least one second database, the generating the at least one vitamin and/or mineral values including selecting, based on the determined category of the food item, a third factor, being different from the first and second factors, in the plurality of factors corresponding to the determined food category, and applying the third factor to determine the at least one vitamin and/or mineral values;

generating, using the at least one processor, at least one controversial ingredient value for the food item based on the executed search query of the at least one first database and analysis of the information obtained from the at least one second database; and generating, using the at least one processor, a nutritional value for the food item based on a combination of the determined calorie value, the determined saturated fat value, the determined unsaturated fat value, the generated vitamin and/or mineral value, and the generated controversial ingredient value, and arranging the generated nutritional value for the food item for display on the graphical user interface.

18. The computer program product according to claim 17, wherein the nutritional value of the food item is determined based on a 2000-calorie diet for the user.

19. The computer program product according to claim 17, wherein the calorie value is determined based on a total number of calories contained in the food item and at least one first factor corresponding to a category of food that includes the food item.

20. The computer program product according to claim 17, wherein the saturated and/or unsaturated fat values are determined based on a total percentage of saturated and/or unsaturated fats contained in the food item and at least one second factor corresponding to a category of food that includes the food item.

21. The computer program product according to claim 17, wherein the vitamins/minerals values are determined based on a total percentage of vitamins/minerals contained in the food item and at least one third factor corresponding to a category of food that includes the food item.

22. The computer program product according to claim 17, wherein the controversial ingredients values are determined based on a number of controversial ingredients contained in the food item and at least one fourth factor corresponding to a category of food that includes the food item.

23. The computer program product according to claim 22, wherein the fourth factor is a constant.

24. The computer program product according to claim 17, wherein the operations further comprise
  determining a value of at least one of the following: a potassium value, a sodium value, a sugar value, a cholesterol value, a carbohydrates value, and a fiber value of the food item;
  wherein the generated nutritional value is generated based on at least one of the following: the determined potassium value, sodium value, sugar value, cholesterol value, carbohydrates value, and fiber value of the food item.

* * * * *